(12) United States Patent
Moffitt

(10) Patent No.: US 10,213,608 B2
(45) Date of Patent: *Feb. 26, 2019

(54) NEUROSTIMULATION SYSTEM WITH FLEXIBLE PATTERNING AND WAVEFORMS

(71) Applicant: Boston Scientific Neuromodulation Corporation, Valencia, CA (US)

(72) Inventor: Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/459,589

(22) Filed: Mar. 15, 2017

(65) Prior Publication Data

US 2017/0182328 A1 Jun. 29, 2017

Related U.S. Application Data

(63) Continuation of application No. 14/789,698, filed on Jul. 1, 2015, now Pat. No. 9,597,517.

(60) Provisional application No. 62/020,836, filed on Jul. 3, 2014.

(51) Int. Cl.
*A61N 1/36* (2006.01)
*A61N 1/372* (2006.01)
*A61N 1/05* (2006.01)

(52) U.S. Cl.
CPC ....... *A61N 1/37247* (2013.01); *A61N 1/0551* (2013.01); *A61N 1/36125* (2013.01); *A61N 1/36175* (2013.01); *A61N 1/36185* (2013.01)

(58) Field of Classification Search
None
See application file for complete search history.

(56) References Cited

U.S. PATENT DOCUMENTS

| | | |
|---|---|---|
| 6,246,912 B1 | 6/2001 | Sluijter et al. |
| 6,516,227 B1 | 2/2003 | Meadows et al. |
| 6,675,046 B2 | 1/2004 | Holsheimer |
| 6,895,280 B2 | 5/2005 | Meadows et al. |
| 6,993,384 B2 | 1/2006 | Bradley et al. |
| 7,076,307 B2 | 7/2006 | Boveja et al. |
| 7,317,948 B1 | 1/2008 | King et al. |
| 7,333,857 B2 | 2/2008 | Campbell |
| 7,539,538 B2 | 5/2009 | Parramon et al. |

(Continued)

FOREIGN PATENT DOCUMENTS

| | | |
|---|---|---|
| CN | 106659884 A | 5/2017 |
| JP | 2009505689 A | 2/2009 |

(Continued)

OTHER PUBLICATIONS

"U.S. Appl. No. 14/789,698, Non Final Office Action dated May 2, 2016", 9 pgs.

(Continued)

*Primary Examiner* — Kennedy Schaetzle
(74) *Attorney, Agent, or Firm* — Schwegman Lundberg & Woessner, P.A.

(57) ABSTRACT

A neurostimulation system configured for providing neurostimulation therapy to a patient. A user customizes a pulse pattern on a pulse-by-pulse basis. Electrical stimulation energy is delivered to at least one electrode in accordance with the customized pulse pattern.

20 Claims, 14 Drawing Sheets

(56) References Cited

U.S. PATENT DOCUMENTS

| | | |
|---|---|---|
| 7,650,184 B2 | 1/2010 | Walter |
| 7,979,133 B2 | 7/2011 | Feler et al. |
| 7,983,762 B2 | 7/2011 | Gliner et al. |
| 8,010,198 B2 | 8/2011 | Libbus et al. |
| 8,019,439 B2 | 9/2011 | Kuzma et al. |
| 8,036,754 B2 | 10/2011 | Lee et al. |
| 8,175,705 B2 | 5/2012 | Libbus |
| 8,224,453 B2 | 7/2012 | De Ridder |
| 8,249,711 B2 | 8/2012 | Libbus et al. |
| 8,255,057 B2 | 8/2012 | Fang et al. |
| 8,340,775 B1 * | 12/2012 | Cullen ............ A61N 1/05 607/2 |
| 8,355,797 B2 | 1/2013 | Caparso et al. |
| 8,401,653 B2 | 3/2013 | Libbus et al. |
| 8,455,716 B2 | 6/2013 | Huang et al. |
| 8,504,147 B2 | 8/2013 | Deem et al. |
| 8,615,300 B2 | 12/2013 | Feler et al. |
| 8,644,947 B2 | 2/2014 | Zhu et al. |
| 8,649,874 B2 | 2/2014 | Alataris et al. |
| 8,660,653 B2 | 2/2014 | Kothandaraman et al. |
| 8,670,831 B2 | 3/2014 | Wacnik et al. |
| 8,676,329 B2 | 3/2014 | Wacnik et al. |
| 8,676,331 B2 | 3/2014 | Parker |
| 8,694,104 B2 | 4/2014 | Libbus et al. |
| 8,706,250 B2 | 4/2014 | Zhu et al. |
| 8,731,675 B2 | 5/2014 | Ranu et al. |
| 8,751,009 B2 | 6/2014 | Wacnik |
| 8,788,048 B2 | 7/2014 | Bennett et al. |
| 8,788,054 B2 | 7/2014 | Kothandaraman et al. |
| 8,909,350 B2 | 12/2014 | Lee |
| 9,138,582 B2 | 9/2015 | Doan |
| 9,174,053 B2 | 11/2015 | Zhu |
| 9,238,138 B2 | 1/2016 | Lee et al. |
| 9,504,838 B2 | 11/2016 | Rao et al. |
| 9,597,517 B2 | 3/2017 | Moffitt |
| 2001/0051787 A1 * | 12/2001 | Haller ............ A61B 5/0031 604/66 |
| 2002/0016617 A1 | 2/2002 | Oldham |
| 2002/0022866 A1 | 2/2002 | Borkan |
| 2002/0143365 A1 | 10/2002 | Herbst |
| 2003/0139781 A1 | 7/2003 | Bradley et al. |
| 2004/0267333 A1 | 12/2004 | Kronberg |
| 2005/0015118 A1 | 1/2005 | Davis et al. |
| 2005/0182456 A1 * | 8/2005 | Ziobro ............ A61B 5/0488 607/48 |
| 2005/0267546 A1 | 12/2005 | Parramon et al. |
| 2006/0149337 A1 | 7/2006 | John |
| 2007/0142874 A1 | 6/2007 | John |
| 2007/0150036 A1 | 6/2007 | Anderson |
| 2008/0188909 A1 | 8/2008 | Bradley |
| 2009/0024189 A1 | 1/2009 | Lee et al. |
| 2009/0204173 A1 | 8/2009 | Fang et al. |
| 2010/0010566 A1 | 1/2010 | Thacker et al. |
| 2010/0121409 A1 | 5/2010 | Kothandaraman et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0054567 A1 * | 3/2011 | Lane ............ A61N 1/08 607/59 |
| 2011/0093041 A1 | 4/2011 | Straka et al. |
| 2012/0059446 A1 | 3/2012 | Wallace et al. |
| 2012/0083709 A1 | 4/2012 | Parker et al. |
| 2012/0215279 A1 | 8/2012 | Libbus |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0004925 A1 * | 1/2013 | Labbe ............ A61N 1/36128 434/262 |
| 2013/0041283 A1 * | 2/2013 | Wichner ............ A61N 1/36 600/547 |
| 2013/0066411 A1 | 3/2013 | Thacker et al. |
| 2013/0116752 A1 | 5/2013 | Parker et al. |
| 2013/0131760 A1 | 5/2013 | Rao et al. |
| 2013/0218239 A1 | 8/2013 | Grill et al. |
| 2013/0268021 A1 | 10/2013 | Moffitt |
| 2013/0296975 A1 | 11/2013 | Lee et al. |
| 2013/0304152 A1 | 11/2013 | Bradley et al. |
| 2014/0081349 A1 | 3/2014 | Lee et al. |
| 2014/0222100 A1 | 8/2014 | Libbus et al. |
| 2014/0257428 A1 | 9/2014 | Zhu |
| 2014/0277267 A1 | 9/2014 | Vansickle et al. |
| 2014/0364920 A1 | 12/2014 | Doan et al. |
| 2015/0134027 A1 | 5/2015 | Kaula et al. |
| 2016/0001087 A1 | 1/2016 | Moffitt |
| 2016/0106985 A1 | 4/2016 | Zhu |
| 2016/0129247 A1 | 5/2016 | Lee et al. |
| 2016/0279422 A1 | 9/2016 | Libbus et al. |
| 2016/0346546 A1 | 12/2016 | Zhu |

FOREIGN PATENT DOCUMENTS

| | | |
|---|---|---|
| JP | 2010534114 A | 11/2010 |
| JP | 2013528416 A | 7/2013 |
| JP | 2017520323 A | 7/2017 |
| WO | WO-2006029257 A2 | 3/2006 |
| WO | WO-2006135791 A2 | 12/2006 |
| WO | WO-2016004230 A1 | 1/2016 |

OTHER PUBLICATIONS

"U.S. Appl. No. 14/789,698, Notice of Allowance dated Nov. 7, 2016", 7 pgs.

"Figure 21-1 The sensory systems encode four elementary attributes of stimuli-modality, location, intensity, and timing-which are manifested in sensation", Principles of Neural Science, Fourth Edition, Kandel, E. R., et al, Editors, McGraw-Hill, (2010), p. 413.

"Figure 22-10 The rate and amplitude of cooling the skin is coded by the firing rates of cold receptors", Principles of Neural Science, Fourth Edition, Kandel, E. R., et al, Editors, McGraw-Hill, (2010), p. 442.

"Figure 22-7 The shape and size of objects touching the hand are encoded by populations of Merkel disk receptors", Principles of Neural Science, Fourth Edition, Kandel, E. R., et al, Editors, McGraw-Hill, (2000), p. 439.

"International Application Serial No. PCT/US2015/038871, International Preliminary Report on Patentability dated Jan. 12, 2017", 6 pgs.

"International Application Serial No. PCT/US2015/038871, International Search Report dated Sep. 11, 2015", 4 pgs.

"International Application Serial No. PCT/US2015/038871, Written Opinion dated Sep. 11, 2015", 4 pgs.

"Australian Application Serial No. 2015284047, First Examiners Report dated Aug. 14, 2017", 3 pgs.

"Canadian Application Serial No. 2,953,578, Office Action dated Oct. 11, 2017", 4 pgs.

"European Application Srial No. 15739421.4, Response filed Sep. 13, 2017 to Communication Pursuant to Rules 161 and 162 EPC dated Mar. 3, 2017", claims not amended at this time, 4 pgs.

"Japanese Application Serial No. 2016-575832, Office Action dated Feb. 5, 2018", w/ English translation, 8 pgs.

\* cited by examiner

NEUROSTIMULATION SYSTEM WITH FLEXIBLE PATTERNING AND WAVEFORMS

CLAIM OF PRIORITY

This application is a continuation of U.S. application Ser. No. 14/789,698, filed Jul. 1, 2015, now issued as U.S. Pat. No. 9,597,517, which claims the benefit of priority under 35 U.S.C. § 119(e) of U.S. Provisional Patent Application Ser. No. 62/020,836, filed on Jul. 3, 2014, each of which is herein incorporated by reference in its entirety.

FIELD OF THE INVENTION

The present invention relates to implantable medical systems, and more particularly, to systems and methods for stimulating tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. A typical stimulation parameter set may include the electrodes that are acting as anodes or cathodes, as well as the amplitude, width, and rate of the stimulation pulses.

Thus, the RC can be used to instruct the neurostimulator to generate electrical stimulation pulses in accordance with the selected stimulation parameters. Typically, the stimulation parameters programmed into the neurostimulator can be adjusted by manipulating controls on the RC to modify the electrical stimulation provided by the neurostimulator system to the patient. Thus, in accordance with the stimulation parameters programmed by the RC, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

The IPG may be programmed by a user, for example, by using a user's programmer (CP), which typically includes a general purpose computer, such as a laptop, with a programming software package installed thereon. Typically, the RC can only control the neurostimulator in a limited manner (e.g., by only selecting a program or adjusting the pulse amplitude or pulse width), whereas the CP can be used to control all of the stimulation parameters, including which electrodes are cathodes or anodes.

The effectiveness of a neurostimulation regimen can best be described in terms of a stimulation capability triad, which includes a spatial component (i.e., stimulating in the right location, which is highly dependent on the disorder to be treated), a temporal component (i.e., stimulating responsive to state, e.g., sensing a relevant physiological parameter and responding with stimulation), and the informational component (i.e., pulsing with patterns to send the right information to stimulate).

With respect to the informational component of the stimulation capability triad, many contemporary neurostimulation systems are programmed with pulse patterns that are either tonic in nature (i.e., a continuous pulse pattern having a uniform pulse rate, pulse width, pulse amplitude, etc. that predictably generates action potentials in the nervous system) or bursted in nature (i.e., a pulse pattern that is alternately turned on and off). However, the human nervous system communicates with the environment using much more sophisticated patterns in which there are encoded many types of information, including pain, pressure, temperature, etc. See Kandel, Schwartz, and Jessell, *Principles of Neural Science*, $4^{th}$ edition, which documents how pulse patterns convey information about the size and shape of different types of mechanical stimuli, convey information how about changes in temperature, and convey information about the initiation and cessation of stimuli. Thus, the nervous system can interpret tonic stimulation as an unnatural phenomenon, which may take the form of paresthesia in some neurostimulation applications.

Some contemporary neurostimulation systems, such as auditory/cochlear stimulation and visual/retinal stimulation devices, are programmed to deliver non-tonic pulse patterns that are interpreted by the nervous stimulation as natural or near-natural phenomenon in the form of proper visual or auditory perception. Recently, there has been extensive research in developing the informational component of the stimulation capability triad to improve the efficacy and efficiency of well-known stimulation applications. For example, non-tonic stimulation involving either high pulse rate and/or quick bursting has been shown to avoid potentially uncomfortable side-effects, such as paresthesia, that typically accompany conventional neurostimulation therapy or pain relief. As another example, some stimulation applications attempt to emulate the natural non-tonic signals that the peripheral nervous system naturally senses in response to external stimuli and transmits to the spinal cord, thereby allowing amputees to sense touch, pressure, and temperature via a robotic arm. As still another example, the brain can be stimulated using more energy efficient non-tonic pulse patterns in order to treat Parkinson's Disease.

While a neurostimulation system can be customized to deliver non-tonic pulse patterns that are appropriate for the application to which the neurostimulation system is to be used, such a customized neurostimulation system would be limited to that particular application and generally not usable for applications using different non-tonic pulse patterns. As such, a neurostimulation system that can be dynamically customizable to deliver any non-tonic pulse pattern within safety limits is needed.

SUMMARY OF THE INVENTION

In accordance with a first aspect of the present inventions, an external control device configured for controlling a neurostimulator implanted within a patient is provided. The external control device comprises a user interface configured for receiving an input from a user, telemetry circuitry configured for communicating with the neurostimulator, and a control circuitry configured for customizing a pulse pattern on a pulse-by-pulse basis in response to the input from the user, and instructing the neurostimulator via the telemetry circuitry to deliver electrical stimulation energy to the patient in accordance with the customized pulse pattern. The neurostimulator may comprise an Application Specific Integrated Circuit (ASIC), in which case, the control circuitry may be configured for programming the ASIC to generate the customized pulse pattern.

The control circuitry may be configured for independently defining the interpulse intervals between adjacent pairs of pulses in the pulse pattern, independently defining the widths of pulses in the pulse pattern, independently defining the amplitudes of pulses in the pulse pattern, independently defining the electrode combinations that deliver pulses in the pulse pattern, and/or adding or subtracting a pulse to or from the pulse pattern in response to the input from the user.

In one embodiment, the control circuitry may be configured for customizing the pulse pattern on the pulse-by-pulse basis by adjusting a multiplicative factor that is applied to a baseline stimulation parameter of the pulse pattern in response to the input from the user. In addition or alternatively, the user interface is configured for displaying the pulse pattern, and the control circuitry is configured for customizing the pulse pattern by allowing the user to drag a portion of the displayed pulse pattern using a pointing element. In addition or alternatively, the control circuitry is configured for limiting the customization of the pulse pattern in accordance with a set of heuristic safety/regulatory rules.

In addition or alternatively, the external control device further comprises memory configured for storing a plurality of different customized pulse patterns, in which case, the control circuitry may be configured for selecting one or more of the customized pulse patterns in response to the input from the user, recalling the selected pulse pattern(s) from the memory, and instructing the neurostimulator via the telemetry circuitry to deliver the electrical stimulation energy in accordance with the recalled pulse pattern(s).

In addition or alternatively, the control circuitry may be configured for customizing another pulse pattern on a pulse-by-pulse basis in response to the input from the user, and instructing the neurostimulator to concurrently deliver the electrical stimulation energy in accordance with the customized pulse pattern and the other customized pulse pattern respectively in two timing channels. In this case, the control circuitry may be configured for defining a phase offset between the customized pulse pattern and the other customized pulse pattern within the respective timing channels in response to the input from the user.

In addition or alternatively, the control circuitry may be configured for globally modifying a stimulation parameter for all pulses of a tonic pulse pattern in response to the input from the user, and for instructing the neurostimulator to deliver the electrical stimulation energy to the patient in accordance with the tonic pulse pattern. In addition or alternatively, the control circuitry may be configured for exporting the customized pulse pattern to a central data base accessible to a plurality of users.

In accordance with a second aspect of the present inventions, a neurostimulation system configured for providing neurostimulation therapy to a patient is provided. The neurostimulation system comprises at least one electrode in contact with tissue of the patient, a neurostimulator configured for delivering electrical stimulation energy to electrode(s), and an external control device configured for allowing a user to customize a pulse pattern on a pulse-by-pulse basis, and instructing the neurostimulator to deliver the electrical stimulation energy to the electrode(s) in accordance with the customized pulse pattern. The neurostimulator may comprise an Application Specific Integrated Circuit (ASIC), in which case, the external control device may be configured for programming the ASIC to generate the customized pulse pattern.

The external control device may be configured for allowing the user to independently define the interpulse intervals between adjacent pairs of pulses in the pulse pattern, allowing the user to independently define the widths of pulses in the pulse pattern, allowing the user to independently define the amplitudes of pulses in the pulse pattern, allowing the user to independently define the electrode combinations that deliver pulses in the pulse pattern, and/or allowing the user to add or subtract a pulse to or from the pulse pattern.

In one embodiment, the external control device may be configured for allowing the user to customize the pulse pattern on the pulse-by-pulse basis by allowing the user to adjust a multiplicative factor that is applied to a baseline stimulation parameter of the pulse pattern. In addition or alternatively, the external control device may be configured for displaying the pulse pattern, and for allowing the user to customize the pulse pattern by allowing the user to drag a portion of the displayed pulse pattern using a pointing element. In addition or alternatively, the external control device may be configured for limiting the customization of the pulse pattern in accordance with a set of heuristic safety/regulatory rules.

In addition or alternatively, the external control device may be configured for storing a plurality of different customized pulse patterns, allowing the user to select one or more of the customized pulse patterns, recalling the selected pulse pattern(s), and instructing the neurostimulator to deliver the electrical stimulation energy in accordance with the recalled o pulse pattern(s).

In addition or alternatively, the external control device may be configured for allowing the user to customize another pulse pattern on a pulse-by-pulse basis, and instructing the neurostimulator to concurrently deliver the electrical stimulation energy in accordance with the customized pulse pattern and the other customized pulse pattern respectively in two timing channels. In this case, the external control device may be configured for allowing the user to define a phase offset between the customized pulse pattern and the other customized pulse pattern within the respective timing channels.

In addition or alternatively, the external control device may be configured for allowing the user to globally modify a stimulation parameter for all pulses of a tonic pulse pattern, and instructing the neurostimulator to deliver the electrical stimulation energy to the electrode(s) in accordance with the tonic pulse pattern. In addition or alternatively, the external control device may be configured for exporting the customized pulse pattern to a central data base accessible to a plurality of users. In addition or alternatively, the neurostimulator is configured for sensing an environmental signal, and the external control device is configured for customizing the pulse pattern on the pulse-by-pulse based on the sensed environmental signal.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
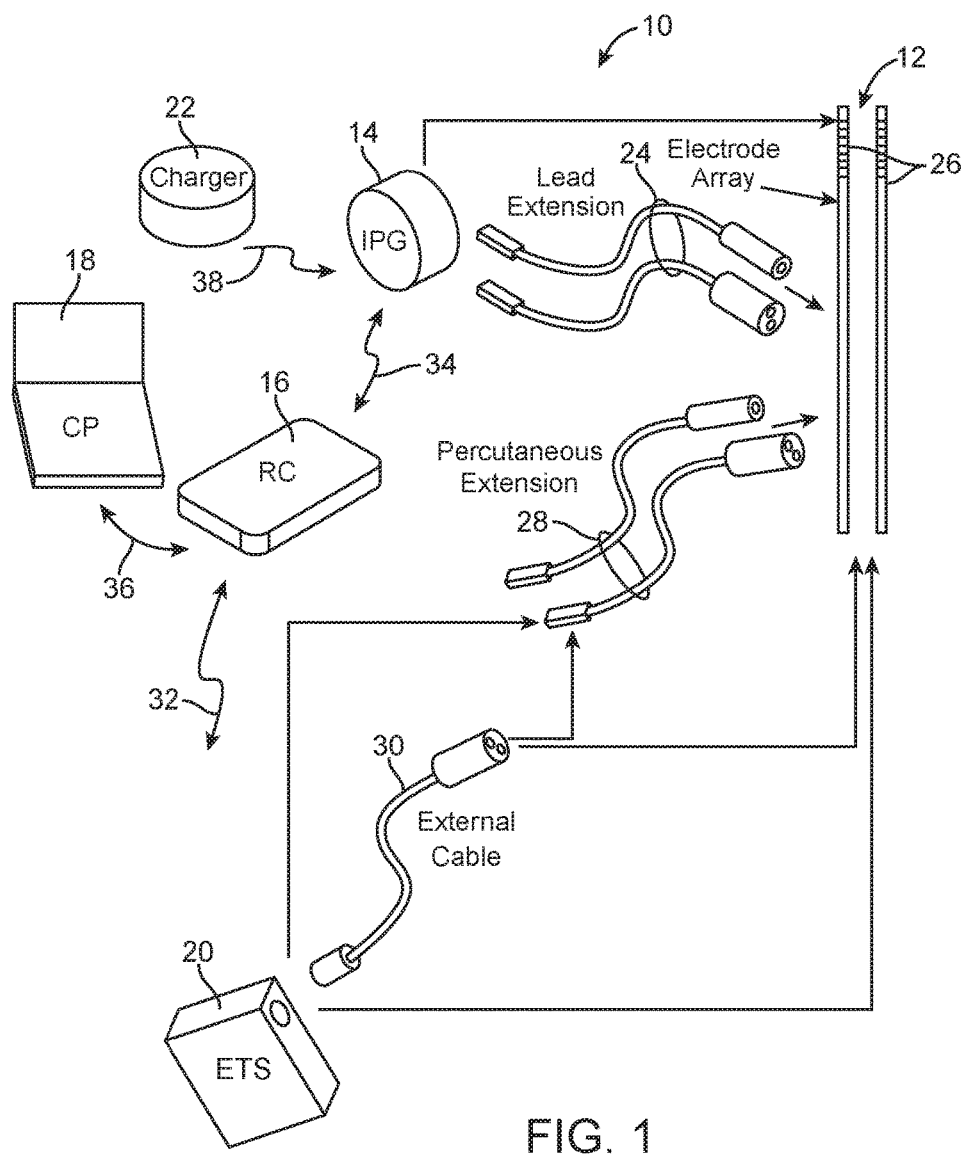
FIG. 1 is plan view of one embodiment of a neurostimulation system arranged in accordance with the present inventions.

Turning first to FIG. 1, an exemplary neurostimulation system 10 constructed in accordance with the present inventions will now be described. The neurostimulation system may be used for neurostimulation application, including SCS, DBS, FES, PNS, ONS, etc. The neurostimulation system 10 generally comprises a plurality of neurostimulation leads 12 (in this case, two percutaneous leads 12a and 12b), an implantable pulse generator (IPG) 14, an external remote control (RC) 16, a User's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides user detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the RC 18, ETS 20, and external charger 22 will not be described herein. Details of exemplary embodiments of these components are disclosed in U.S. Pat. No. 6,895,280, which is expressly incorporated herein by reference.

Figure 2:
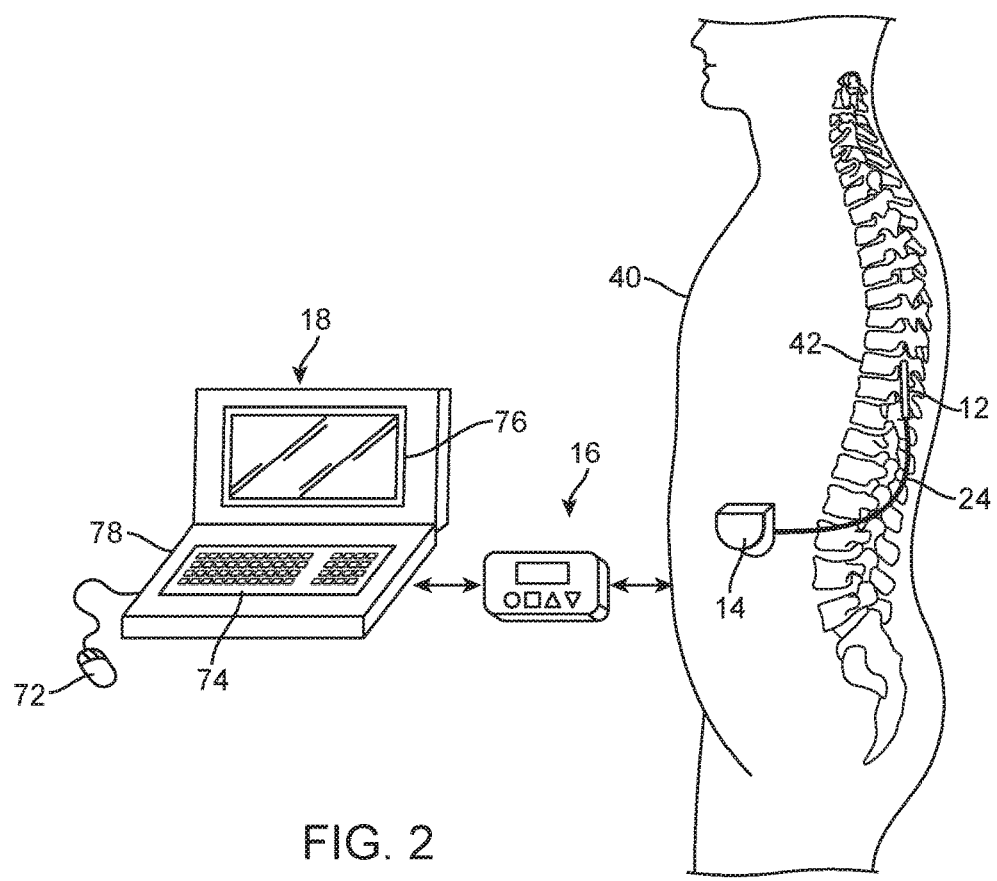
FIG. 2 is a plan view of the neurostimulation system of FIG. 1 in use to perform spinal cord stimulation (SCS) on a patient.

Referring to FIG. 2, if the neurostimulation system 10 is used to perform SCS, the neurostimulation leads 12 are implanted at an initial position within the spinal column 42 of a patient 40. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. After implantation, the IPG 14 can be operated to generate a volume of activation relative to the target tissue to be treated, thereby providing the therapeutic stimulation under control of the patient.

Figure 3:
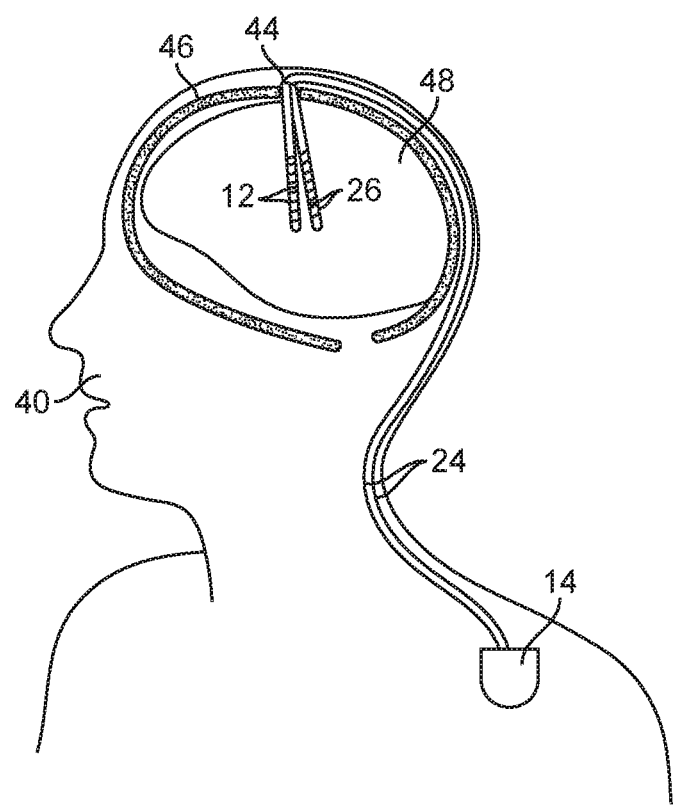
FIG. 3 is a plan view of the neurostimulation system of FIG. 1 in use to perform deep brain stimulation (DBS) on a patient.

Referring to FIG. 3, if the neurostimulation system 10 is used to perform DBS, two neurostimulation leads 12 are introduced through a burr hole 44 (or alternatively, two respective burr holes) formed in the cranium 46 of the patient 40, and introduced into the parenchyma of the brain 48 of the patient 40 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 44, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

More significant to the present inventions, the neurostimulation system 10 allows a user to program, save, and import/export sophisticated pulse pattern patterns, which enables unique information to be delivered to the nervous system, which as described in the background, uses action potentials having patterns that are much more sophisticated than the pulse patterns that are generated by conventional neurostimulation systems.

To this end, the neurostimulation system 10 is capable of allowing a user to customize pulse patterns on a pulse-by-pulse basis, meaning that at least one stimulation parameter associated with each pulse or interpulse interval between adjacent pulses independent of other pulses or interpulse intervals in the pulse pattern. In this manner, the pulse patterns may be defined in an arbitrary manner. The electrical stimulation energy can then be delivered to the electrodes 26 in accordance with one of these customized pulse patterns, thereby more effectively and/or efficiently treating the particular ailment to which the customization of the pulse pattern is designed.

Figure 4:
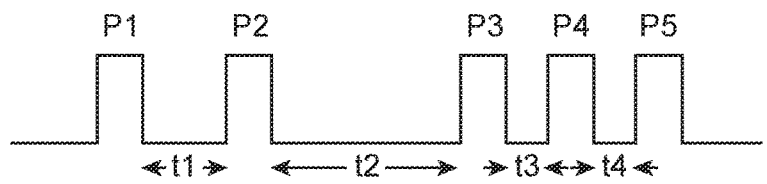
FIG. 4 is a timing diagram of one pulse pattern having interpulse intervals that can be customized on a pulse-by-pulse basis using the neurostimulation system of FIG. 1.

In one technique for customizing a pulse pattern, the interpulse intervals (IPIs) of the pulse pattern may be independently defined between adjacent pairs of pulses in the pulse pattern. For example, as illustrated in FIG. 4, the interpulse interval between pulses P1 and P2 may be defined by time interval t1, the interpulse interval between pulses P2 and P3 may be defined by time interval t2 that is greater than time interval t1, and the interpulse intervals between pulses P3 and P4 and between P4 and P5 may be defined by equal time intervals t3 and t4, which are smaller than time intervals t1 and t2.

Figure 5:
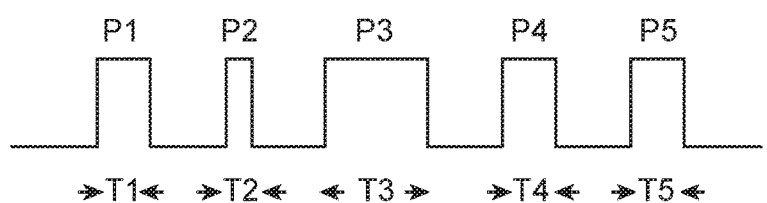
FIG. 5 is a timing diagram of another pulse pattern having pulse widths that can be customized on a pulse-by-pulse basis using the neurostimulation system of FIG. 1.

In another technique for customizing a pulse pattern, the widths of the pulses in the pulse pattern may be independently defined. For example, as illustrated in FIG. 5, the width of pulse P1 may be defined by time duration T1, the width of pulse P2 may be defined by time duration T2, which is smaller than time duration T1, the width of pulse P3 may be defined by time duration T3, which is greater than both time durations T1 and T2, the width of pulse P4 may be defined by time duration T4, which is equal to time duration T1, and the width of pulse P5 may be defined by time duration T5, which is equal to both time durations T1 and T5.

Figure 6:
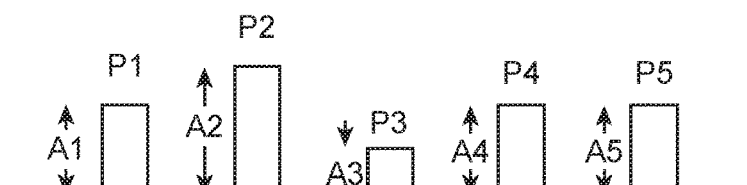
FIG. 6 is a timing diagram of still another pulse pattern having pulse amplitudes that can be customized on a pulse-by-pulse basis using the neurostimulation system of FIG. 1.

In still another technique for customizing a pulse pattern, the amplitudes of the pulses in the pulse pattern may be independently defined. For example, as illustrated in FIG. 6, the amplitude of pulse P1 may be defined as amplitude A1, the amplitude of pulse P2 may defined as amplitude A2, which is greater than amplitude A1, the amplitude of pulse P3 may be defined as amplitude A3, which is less than amplitudes A1 and A2, the amplitude of pulse P4 may be defined as amplitude A4, which is equal to amplitude A1, and the amplitude of pulse P5 may be defined as amplitude A5, which is equal to amplitudes A1 and A4.

Figure 7:
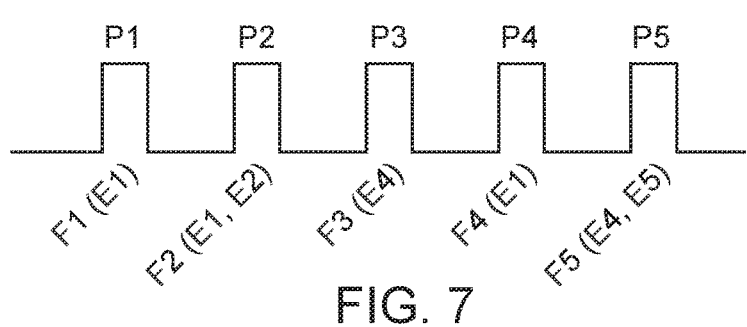
FIG. 7 is a timing diagram of yet another pulse pattern having pulse fields that can be customized on a pulse-by-pulse basis using the neurostimulation system of FIG. 1.

In yet another technique for customizing a pulse pattern, the electrode combinations that deliver pulses in the pulse pattern can be independently defined to generate different electrical fields for the respective pulses. For example, as illustrated in FIG. 7, electrode E1 can be used to deliver pulse P1 to generate electrical field F1, electrodes E1, E2 can be used to deliver pulse P2 to generate electrical field F2, electrode E4 can be used to deliver pulse P3 to generate electrical field F3, electrode E1 can be used to deliver pulse P4 to generate electrical field F4, which will be the same as electrical field F1, and electrodes E4 and E5 can be used to deliver pulse P5 to generate electrical field F5.

In yet another embodiment for customizing a pulse pattern, the shapes of the pulses in the pulse pattern may be independently defined. For example, any pulse can be defined as a square pulse, an exponential pulse, a logarithmic pulse, a ramped pulse, trapezoidal pulse, or any arbitrary shape. Further detail discussing defining the pulse shape of a pulsed waveform are set forth in U.S. Pat. No. 8,036,754, which is expressly incorporated herein by reference.

Figure 8:
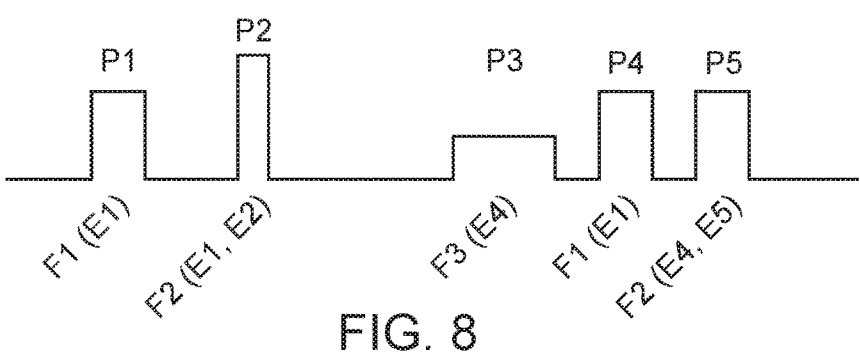
FIG. 8 is a timing diagram of yet another pulse pattern having intervals, pulse widths, pulse amplitudes, and pulse fields that can be customized on a pulse-by-pulse basis using the neurostimulation system of FIG. 1.

It should be appreciated that although only one stimulation parameter for each pulse pattern is shown as being independently defined on a pulse-by-pulse basis in FIGS. 4-7, any number of different stimulation parameters can be independently defined on a pulse-by-pulse basis. For example, as illustrated in FIG. 8, the interpulse intervals, pulse widths, pulse amplitudes, and electrode combinations are independently defined by pulses P1-P5.

Figure 9:
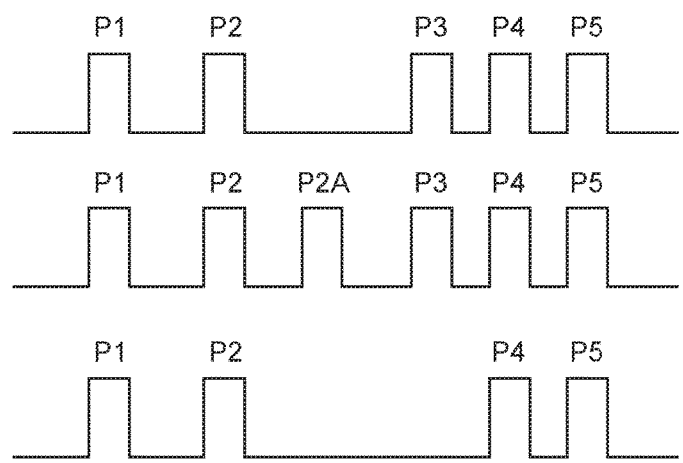
FIG. 9 is a timing diagram of pulse patterns that can be customized with added or subtracted pulses using the neurostimulation system of FIG. 1.

It should also be appreciated that although the stimulation parameter(s) associated with pre-existing pulses of the pulse patterns have been described as being independently defined with respect to FIGS. 4-8, pulses may be independently added or subtracted anywhere within or from a pulse pattern. For example, as illustrated in FIG. 9, pulse P2a can be added to the pulse pattern between pulses P2 and P3, or pulse P3 can be subtracted from the pulse pattern. Of course, the pulse patterns can be customized in the manner described in FIGS. 4-8 prior to or after the pulses are added to or subtracted from the pulse patterns.

Figure 10:
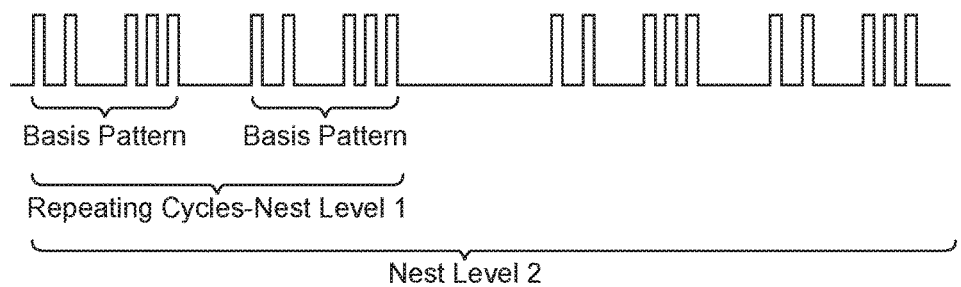
FIG. 10 is a timing diagram of a nested pulse pattern that can be customized using the neurostimulation system of FIG. 1.

The number of pulses that can be independently varied in a pulse pattern may be any value, e.g., in the range of 2-1000 independently variable pulses. The pattern of pulses in any particular waveform may repeated in nested cycle times, as illustrated in FIG. 10. In particular, a five pulse basis pattern can be repeated twice at a Nest Level 1 to create a combined ten-pulse pattern, and this ten-pulse pattern can be repeated an indefinite number of times at a Nest Level 2. The time period t1 between the five-pulse basis patterns at Next Level 1 can be defined by the user, and the time period t2 between the combined ten-pulse patterns can be defined by the user. This pulse pattern can be expanded to additional nest levels.

Figure 11:
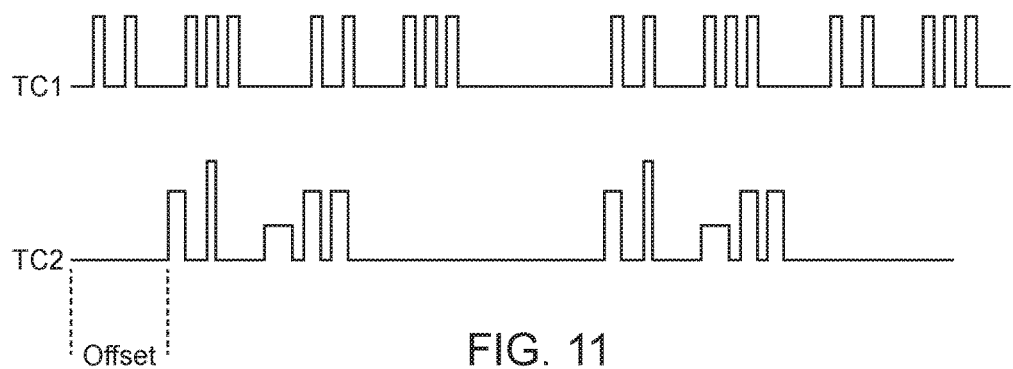
FIG. 11 is a timing diagram of two customized pulse patterns having an offset between two timing channels that can be customized using the neurostimulation system of FIG. 1.

Although a single customized pulse pattern is shown as being delivered in FIGS. 4-10, the neurostimulation system 10 may deliver multiple customized pulse patterns or a combination of customized and conventional pulse patterns in multiple timing channels. For example, as illustrated in FIG. 11, two customized pulse patterns are concurrently delivered in two timing channels TC1 and TC2. The neurostimulation system 10 allows the user to define a phase offset between the pulse patterns.

To ensure that the user does not customize a pulse pattern in the manner that may cause harm to the patient and/or the electrodes 26, the neurostimulation system 10 is configured for limiting the customization of each pulse pattern in accordance with a set of heuristic safety/regulatory rules. For example, the neurostimulation system 10 may have a minimum interpulse interval that corresponds to the maximum effective pulse rate, may require the timing channels to utilize independent electrodes or other resource-sharing rules, may require the cumulative charge to remain below a maximum (e.g., 12.7 µC), may require the cumulative charge to cross-zero within a minimum time (e.g., a value between 4 to 10 ms), or may require an active or passive discharge phase for each pulse to avoid accumulation of charge.

The neurostimulation system 10 is capable of storing different customized pulse patterns, allowing the user to select one of the stored customized pulse patterns, recalling the selected pulse pattern, and delivering the electrical stimulation energy in accordance with the recalled pulse pattern. The neurostimulation system 10 optionally has import/export capability that allows users to share the customized pulse patterns with each other from a central database. The neurostimulation system 10 also optionally may be configured for sensing an environmental signal (e.g., a physiological signal), and customizing a pulse pattern on a pulse-by-pulse basis based on the sensed environmental signal, or changing between pre-configured pulse patterns based on the external signal or information derived from the signal. Although the neurostimulation system 10 has only been described as allowing the user to customize pulse patterns on a pulse-by-pulse basis, the neurostimulation system 10 is also capable of conventionally allowing the user to globally modify a stimulation parameter for all pulses of a tonic pulse pattern, in which case, the neurostimulation system 10 will deliver the electrical stimulation energy to the electrodes 26 in accordance with the tonic pulse pattern.

Figure 12:
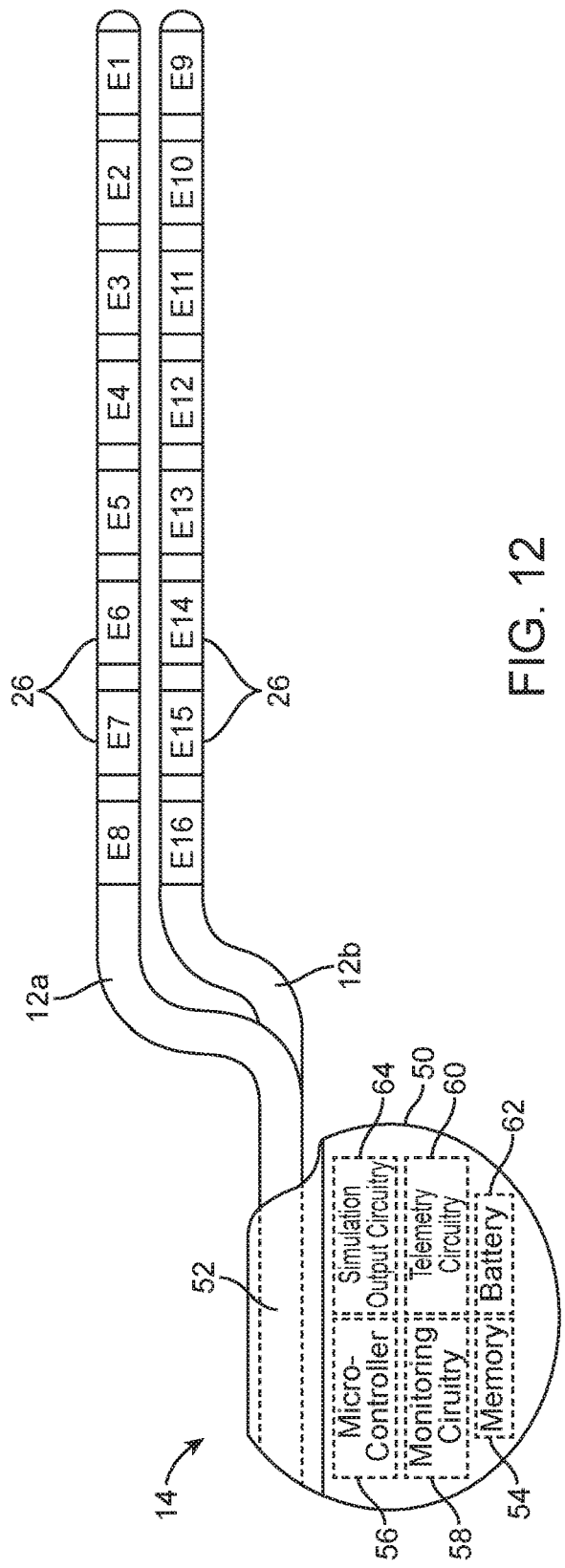
FIG. 12 is a side view of an implantable pulse generator and a pair of percutaneous neurostimulation leads that can be used in the neurostimulation system of FIG. 1.
Figure 13:
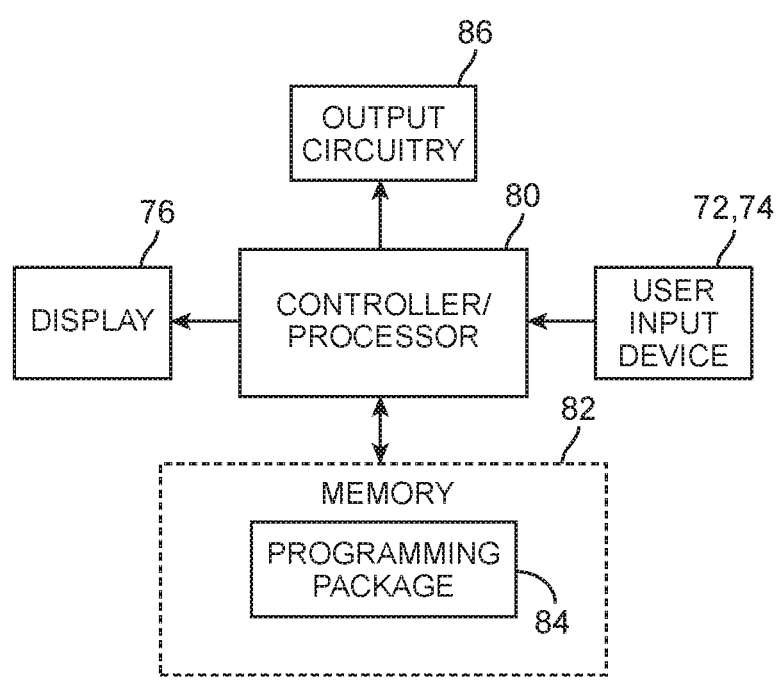
FIG. 13 is a block diagram of the internal components of a clinician's programmer (CP) used in the neurostimulation system of FIG. 1.

Referring now to FIG. 12, the external features of the neurostimulation leads 12a, 12b and the IPG 14 will be briefly described. Each of the neurostimulation leads 12 has eight electrodes 26 (respectively labeled E1-E8 for the lead 12a and E9-E16 for the lead 12b). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 50 for housing the electronic and other components (described in further detail below). The outer case 50 is composed of an electrically conductive, biocompatible material, such as titanium, and forms a hermetically sealed compartment wherein the internal electronics are protected from the body tissue and fluids. In some cases, the outer case 50 may serve as an electrode. The IPG 14 further comprises a connector 52 to which the proximal ends of the neurostimulation leads 12 mate in a manner that electrically couples the electrodes 26 to the internal electronics (described in further detail below) within the outer case 50. To this end, the connector 52 includes two ports (not shown) for receiving the proximal ends of the leads 12. In the case where the lead extensions 24 are used, the ports may instead receive the proximal ends of such lead extensions 24.

As briefly discussed above, the IPG 14 includes circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y). As will be described in further detail below, the IPG 14 also includes circuitry that provides electrical signals, and measured electrical impedance in response to the electrical signals.

With respect to the pulsed electrical waveform provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the LPG case 50, so that the electrical current has a path from the energy source contained within the IPG case 50 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 50 of the IPG 14, so that electrical energy is transmitted between the selected electrode 26 and case 50. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The IPG 14 comprises electronic components, such as a memory 54, controller/processor (e.g., a microcontroller) 56, monitoring circuitry 58, telemetry circuitry 60, a battery 62, stimulation output circuitry 64, and other suitable components known to those skilled in the art.

The memory 54 is configured for storing programming packages, stimulation parameters (including customized pulse patterns), measured physiological information, and other important information necessary for proper functioning of the LPG 14. The microcontroller 56 executes a suitable program stored in memory 54 for directing and controlling the neurostimulation performed by IPG 14. The monitoring circuitry 58 is configured for monitoring the status of various nodes or other points throughout the IPG 14, e.g., power supply voltages, temperature, battery voltage, and the like. Notably, the electrodes 26 fit snugly within the patient, and because the tissue is conductive, electrical measurements can be taken between the electrodes 26. Thus, the monitoring circuitry 58 is configured for taking such electrical measurements (e.g., electrode impedance, field potential, evoked action potentials, etc.) for performing such functions as detecting fault conditions between the electrodes 26 and the stimulation output circuitry 64, determining the coupling efficiency between the electrodes 26 and the tissue, determining the posture/patient activity of the patient, facilitating lead migration detection, etc., and more significant to the present inventions, customizing pulse patterns, sensing of physiological signals such as local field potentials or single unit action potentials.

The telemetry circuitry 60, including an antenna (not shown), is configured for receiving programming data (e.g., the operating program and/or stimulation parameters, including pulse patterns) from the RC 16 and/or CP 18 in an appropriate modulated carrier signal, which the programming data is then stored in the memory 54. The telemetry circuitry 60 is also configured for transmitting status data and sensed physiological data to the RC 16 and/or CP 18 in an appropriate modulated carrier signal. The battery 62, which may be a rechargeable lithium-ion or lithium-ion polymer battery, provides operating power to IPG 14. The stimulation output circuitry 64 is configured for, under control of the microcontroller 56, generating and delivering electrical energy, in the form of electrical pulse trains, to each of the electrodes 26, as well as any electrical signals needed for acquiring electrical measurements. To accommodate the generation of stimulation energy in accordance with the customized pulse patterns, the stimulation output circuitry 64 may comprise an Application Specific Integrated Circuit (ASIC), in which case, the microcontroller 56 may program the ASIC to generate the customized pulse patterns. Alternatively, the microcontroller 56 may continually or frequently communicate with the stimulation output circuitry 64 to generate the customized pulse patterns, although this latter arrangement may expend more energy.

Notably, while the microcontroller 56 is shown in FIG. 12 as a single device, the processing functions and controlling functions can be performed by a separate controller and processor. Thus, it can be appreciated that the controlling functions performed by the IPG 14 can be performed by a controller, and the processing functions performed by the IPG 14 can be performed by a processor. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-modulator (not shown) connected to the leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the stimulation in accordance with the control signals.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry (not shown) that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

In some cases described below, the pointing device can be used to select and drag a graphical element. The manner in which the graphical element is selected and dragged will depend on the nature of the user interface.

For example, when employing a conventional display screen 76 in conjunction with a mouse 72 or other pointing device, the user may select the graphical element by, e.g., placing the cursor over the graphical element and clicking or pressing the appropriate button of the mouse 72. The user can then move the cursor to drag the graphical element within the programming screen, thereby moving the graphical representation to a desired location on the display. Once the graphical element is positioned as desired, the user can release the mouse button, thereby fixing the graphical element at the desired location.

Alternatively for a touchscreen, also known as a digitizer screen, a stylus or finger is used, and the user may select the graphical element by, e.g., physically touching the screen where the graphical element is located. The user can drag the graphical element by moving the stylus/finger across the programming screen, finally fixing the graphical element at a desired location.

Figure 14:
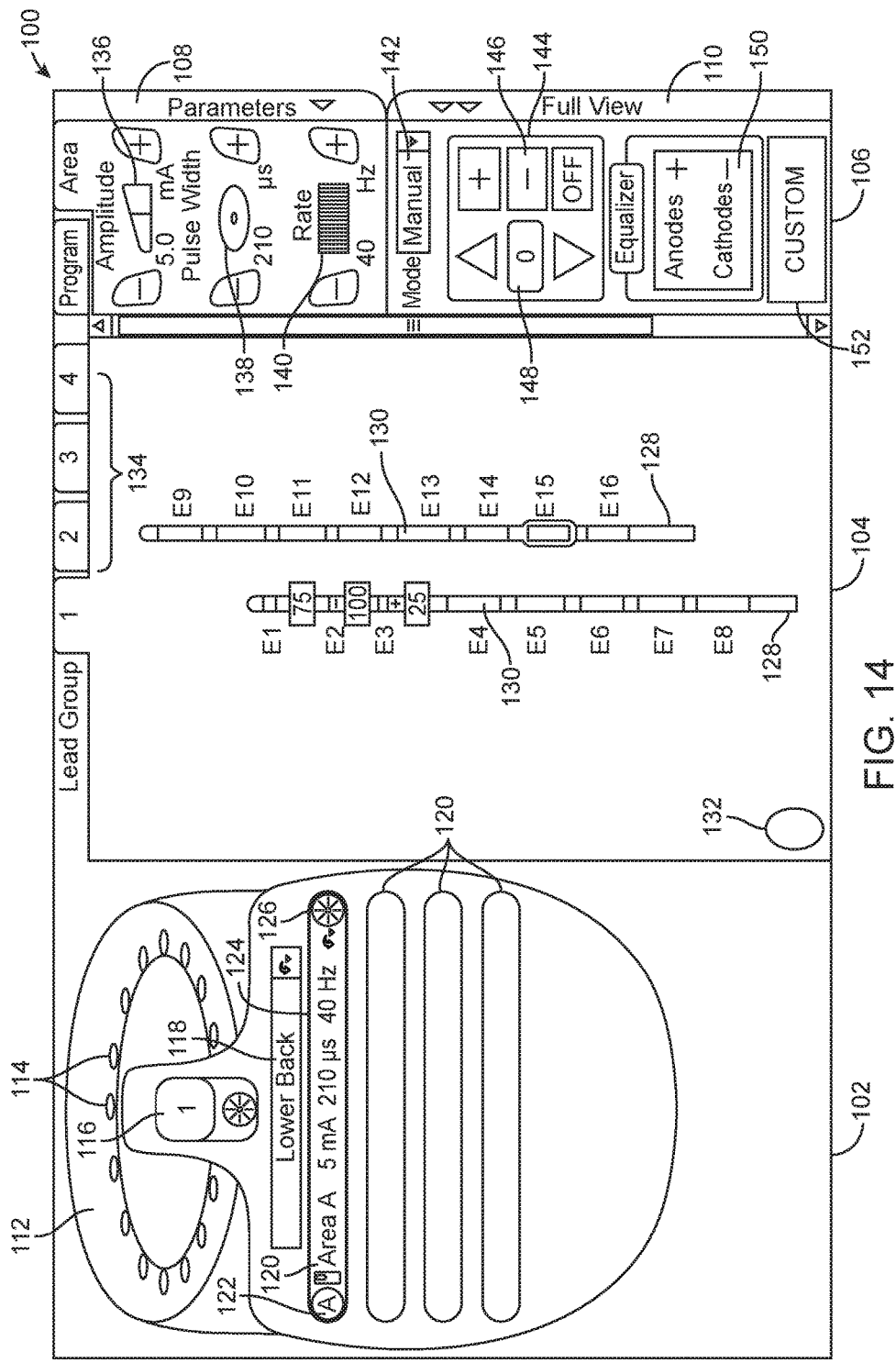
FIG. 14 is a plan view of a programming screen of the CP of FIG. 13 for programming the IPG of FIG. 12.

As shown in FIG. 14, the CP 18 generally includes control/processing circuitry 80 (e.g., a central processor unit (CPU)) and memory 82 that stores a stimulation programming package 84, which can be executed by the control/processing circuitry 80 to allow the user to program the IPG 14, and RC 16. The CP 18 further includes input/output circuitry 86 for downloading stimulation parameters to the IPG 14 and RC 16 and for uploading stimulation parameters already stored in the memory 66 of the IPG 14 or RC 16.

Execution of the programming package 84 by the control/processing circuitry 80 provides a multitude of display screens (not shown) that can be navigated through via use of the mouse 72. These display screens allow the user to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Referring first to FIG. 14, a programming screen 100 that can be generated by the CP 18 to allow a user to program the IPG 14 will be described. In the illustrated embodiment, the programming screen 100 comprises three panels: a program selection panel 102, a lead display panel 104, and a stimulation parameter adjustment panel 106. Some embodiments of the programming screen 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about stimulation programs and coverage areas that have been, or may be, defined for the IPG 14. In particular, the program selection panel 102 includes a carousel 112 on which a plurality of stimulation programs 114 (in this case, up to sixteen) may be displayed and selected. The program selection panel 102 further includes a selected program status field 116 indicating the number of the stimulation program 114 that is currently selected (any number from "1" to "16"). In the illustrated embodiment, program 1 is the only one currently selected, as indicated by the number "1"

in the field 116. The program selection panel 102 further comprises a name field 118 in which a user may associate a unique name to the currently selected stimulation program 114. In the illustrated embodiment, currently selected program 1 has been called "lower back," thereby identifying program 1 as being the stimulation program 114 designed to provide therapy for lower back pain.

The program selection panel 102 further comprises a plurality of coverage areas 120 (in this case, up to four) with which a plurality of stimulation parameter sets can respectively be associated to create the currently selected stimulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the stimulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the stimulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective stimulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a stimulation parameter set. Once selected, the coverage area 120 will be populated with the designation field 122, electrical pulse parameter field 124, and selection icon 126.

The lead display panel 104 includes graphical leads 128, which are illustrated with eight graphical electrodes 130 each (labeled electrodes E1-E8 for the first lead 128 and electrodes E9-E16 for second lead 128). The lead display panel 104 also includes a graphical case 132 representing the case 44 of the IPG 14. The lead display panel 104 further includes lead group selection tabs 134 (in this case, four) corresponding to the four coverage areas 120, any of which can be actuated to select one of four groups of graphical leads 128. In this case, the first lead group selection tab 134 has been actuated, thereby displaying the two graphical leads 128 in their defined orientation. In the case where additional leads 12 are implanted within the patient, they can be associated with additional lead groups.

The parameters adjustment panel 106 also includes a pulse amplitude adjustment control 136 for adjusting the amplitude of the pulses (expressed in milliamperes (mA)), a pulse width adjustment control 138 for adjusting the width of the pulses (expressed in microseconds (μs)), and a pulse rate adjustment control 140 for adjusting the rate of the pulses (expressed in Hertz (Hz)), which are displayed and actuatable in all the programming modes. Each of the controls 136-140 includes a first arrow that can be actuated to decrease the value of the respective stimulation parameter and a second arrow that can be actuated to increase the value of the respective stimulation parameter. Each of the controls 136-140 also includes a display area for displaying the currently selected parameter.

The parameter adjustment panel 106 includes a pull-down programming mode field 142 that allows the user to switch between a manual programming mode, and an electronic trolling programming mode. Each of these programming modes allows a user to define a stimulation parameter set for the currently selected coverage area 120 of the currently selected program 114 via manipulation of graphical controls in the parameter adjustment panel 106 described above. The manual programming mode is designed to allow the user to manually define the fractionalized electrical current for the electrode array with maximum flexibility; the electronic trolling programming mode is designed to quickly sweep the electrode array using a limited number of electrode configurations to gradually steer an electrical field relative to the neurostimulation leads until the targeted stimulation site is located, and the navigation programming mode is designed to sweep the electrode array using a wide number of electrode configurations to shape the electrical field, thereby fine tuning and optimization the stimulation coverage for patient comfort.

As shown in FIG. 14, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104.

In the illustrated embodiment, electrode E2 has been selected as a cathode to which 100% of the cathodic current has been allocated, and electrodes E1 and E3 have been respectively selected as anodes to which 25% and 75% of the anodic current has been respectively allocated. Electrode E15 is shown as being selected to allow the user to subsequently allocate the polarity and fractionalized electrical current to it via the graphical controls located in the amplitude/polarity area 144. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameters adjustment panel 106, when the manual programming mode is selected, also includes an equalization control 150 that can be actuated to automatically equalize current allocation to all electrodes of a polarity selected by respective "Anode +" and "Cathode −" icons. Further details discussing the electronic trolling programming mode and navigation programming mode are set forth in U.S. Pat. No. 8,660,653, which is expressly incorporated herein by reference.

Figure 15:
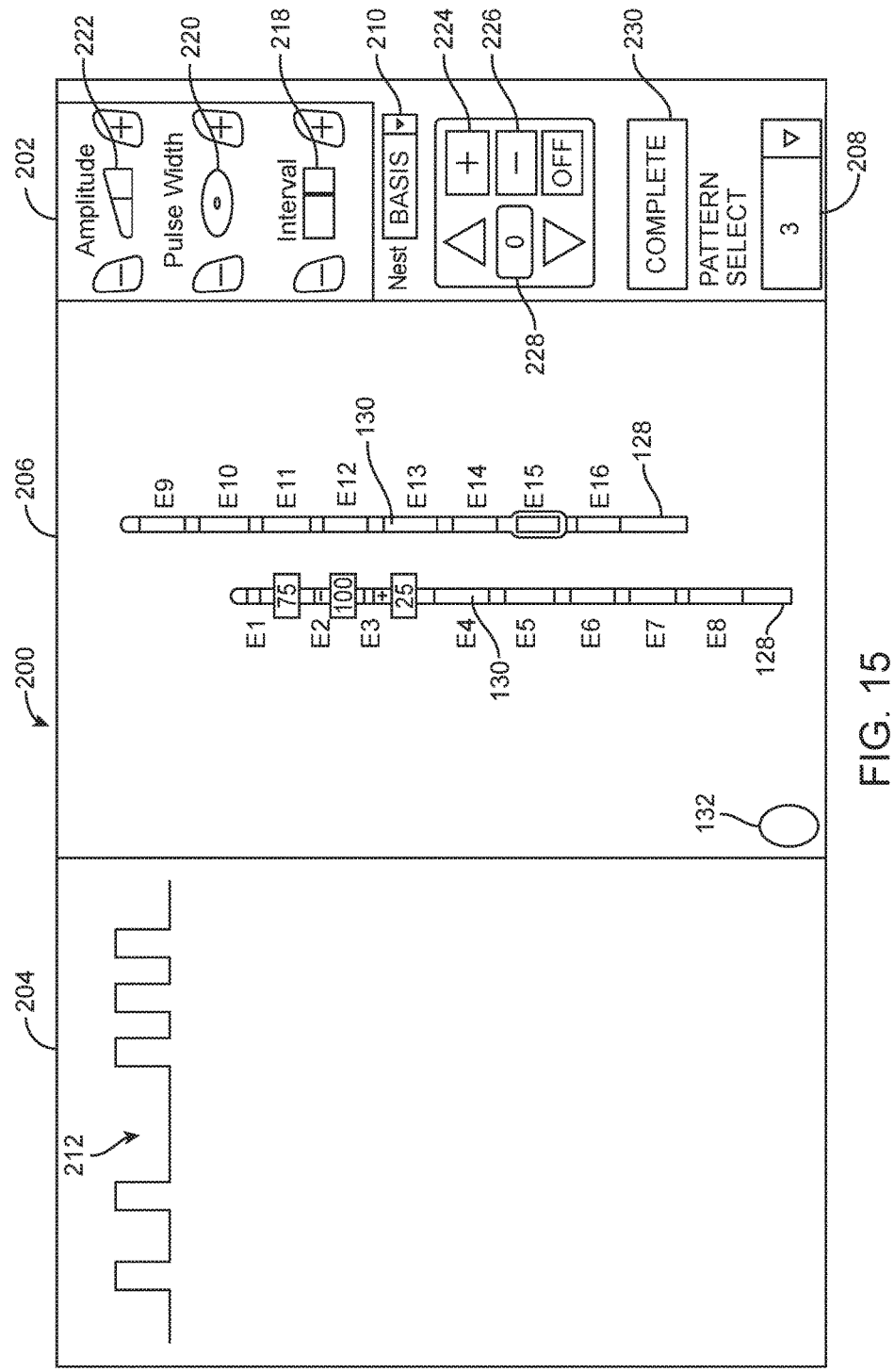
FIG. 15 is a plan view of a programming screen of the CP of FIG. 13 for customizing pulse pattern, wherein a basis pulse pattern has been selected for customization.

Significant to the present inventions, the parameter adjustment panel 106 also comprises a custom pulse pattern control 152 that can be actuated to allow the user to customize one or more pulse patterns. When the custom pulse pattern control 152 is actuated, the user is automatically taken to custom pulse pattern screen 200 as shown in FIG. 15. The custom pulse pattern screen 200 allows the user to customize a maximum number of sixteen pulse patterns, although any number of pulse patterns may be customized, including only one.

In the illustrated embodiment, the custom pulse pattern screen 200 includes a pulse pattern customization panel 202, a pulse pattern display panel 204, and a lead display panel 206. The pulse pattern customization panel 202 includes a pulse pattern selection menu 208 that can be actuated to select any one of a number of stored custom pulse patterns. In the illustrated embodiment, a maximum number of sixteen custom pulse patterns may be generated and stored for subsequent selection, although, in alternative embodiments, any number of custom pulse patterns may be generated and stored, including only one custom pulse pattern. Upon selection of a custom pulse pattern via the menu 208, the selected pulse pattern will be displayed in the pulse pattern display panel 204 and associated with the coverage 120 that was currently selected in the programming screen 100 when the custom pulse pattern control 152 was actuated (see FIG. 14). Any of the selected custom pulse patterns may be modified as described below.

Figure 16:
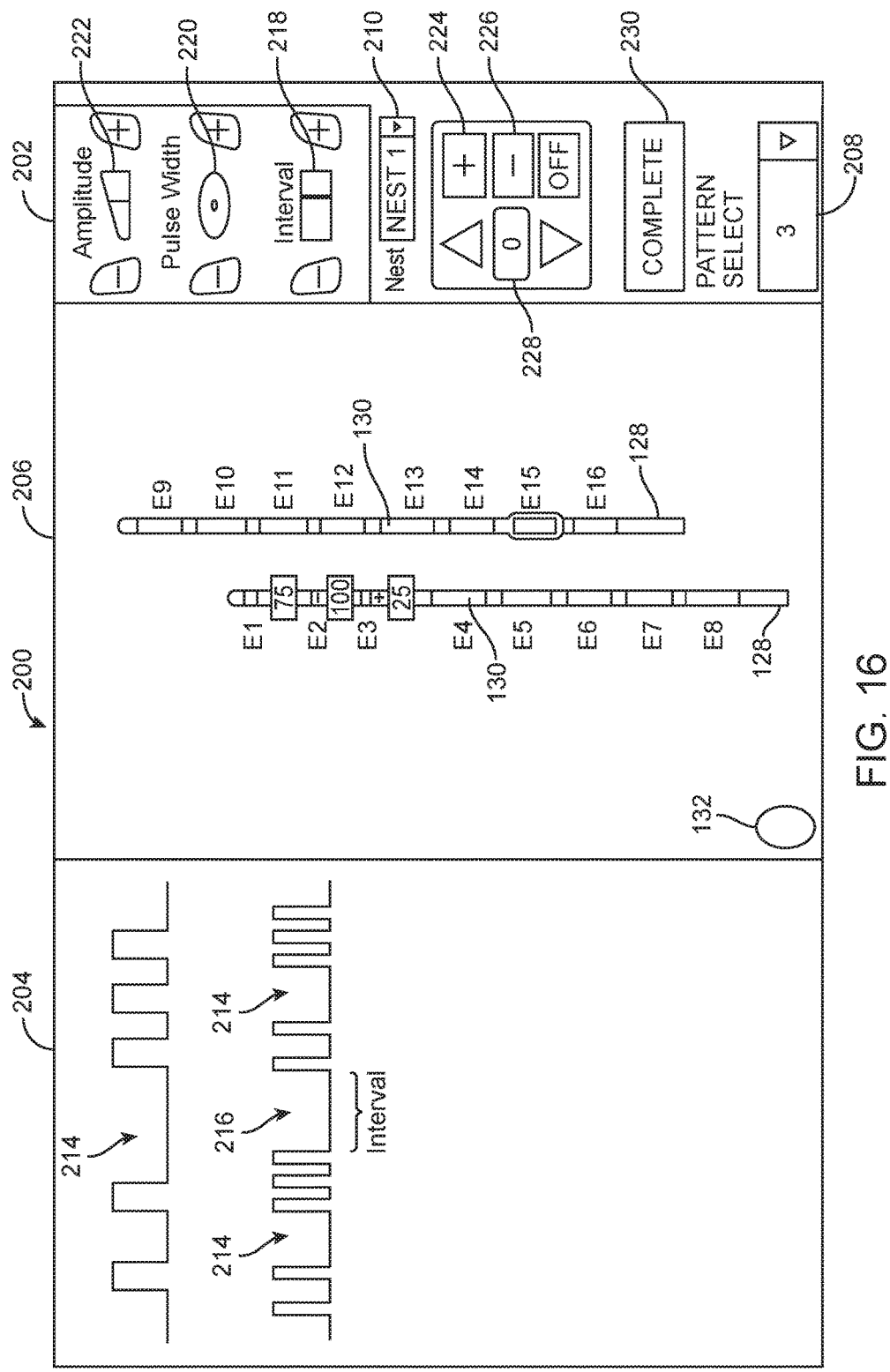
FIG. 16 is a plan view of the programming screen of FIG. 15, wherein a repeating pulse pattern has been selected for customization.

The pulse pattern customization panel 202 further includes a pulse nesting menu 210 that can be actuated to select between a basis pulse pattern, a first nest, and a second nest. Selection of the basis pulse pattern via the pulse nesting menu 210 allows the user to modify the parameters of the pulse pattern on a pulse-by-pulse manner to define a group of adjacent pulses that can be referred to as a basis pulse pattern 212, which can be displayed in the pulse pattern display panel 204, as illustrated in FIG. 15. Selection of the first nest allows the user to modify the time periods between cyclically repeating basis pulse patterns 212 of a repeating pulse pattern 214, as illustrated in FIG. 16. Selection of the second nest allows the user to modify the time periods between cyclically repeating pulse patterns 214 of a complete pulse pattern 216, as illustrated in FIG. 17.

Figure 17:
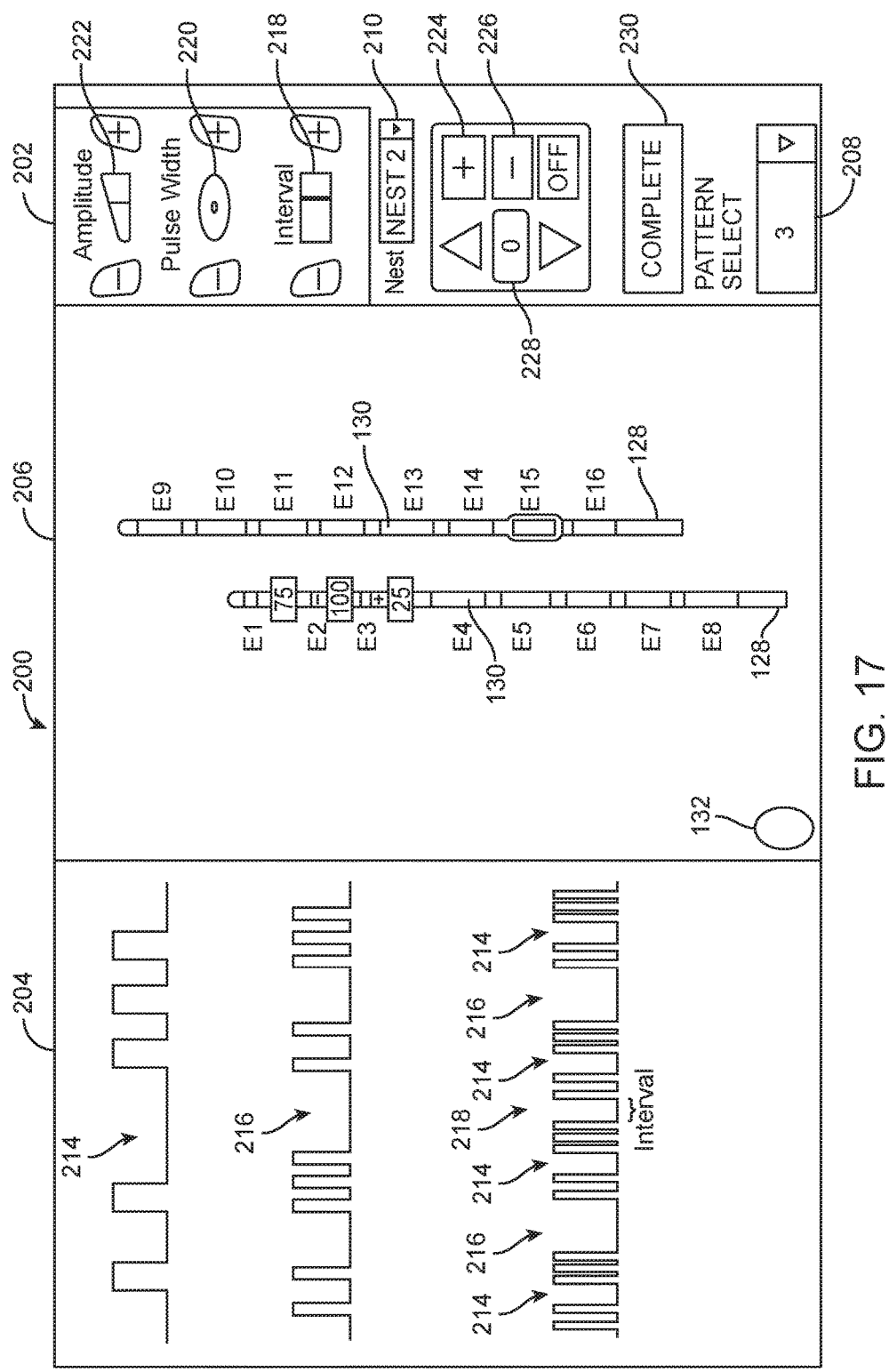
FIG. 17 is a plan view of the programming screen of FIG. 15, wherein a combined pulse pattern has been selected for customization.

The pulse customization panel 202 also includes a multitude of controls for individually modifying the parameters of a selected pulse or interpulse interval of the basis pulse pattern 212 (FIG. 15), or the interval between basis pulse patterns 212 within the repeating pulse pattern 214 (FIG. 16), or the interval between the cyclically repeating pulse patterns 212 of the complete pulse pattern 216 (FIG. 17).

In particular, the pulse customization panel 202 includes a time interval adjustment control 218 for adjusting a selected interpulse interval (if the basis pulse pattern has been selected via the pulse nesting menu 210), a selected time interval between adjust basis pulse pattern (if the first nest has been selected via the pulse nesting menu 210), and a selected time interval between adjacent groups of basis pulse patterns (if the second nest has been selected via the pulse nesting menu 210 (expressed in milliseconds (ms)). The pulse customization panel 202 further includes a pulse width adjustment control 220 for adjusting the width of a selected pulse (expressed in microseconds (μs)), and a pulse amplitude adjustment control 222 for adjusting the magnitude of a selected pulse (expressed in milliamperes (mA)).

Each of the controls 218-222 includes a first arrow that can be actuated to decrease the value of the respective parameter and a second arrow that can be actuated to increase the value of the respective parameter. Each of the controls 218-222 also includes a display area for displaying the currently selected parameter. In the illustrated embodiment, the particular pulse or time interval that is currently modified using the controls 218-222 may be selected in the pulse pattern display panel 204 using the appropriate pointing device.

The resolution of each of the controls 218-222 may be finer than the minimum expected value of the respective parameter, or may be equal to a minimum baseline value of the respective parameter, in which case, each of the controls 218-222 may allow the user to adjust a multiplicative factor of the minimum baseline value. For example, if the minimum base line value of a pulse width is 50 μs, the pulse width adjustment control 220 may be actuated to adjust the pulse width of a selected pulse in increments of 50 μs.

Figure 18:
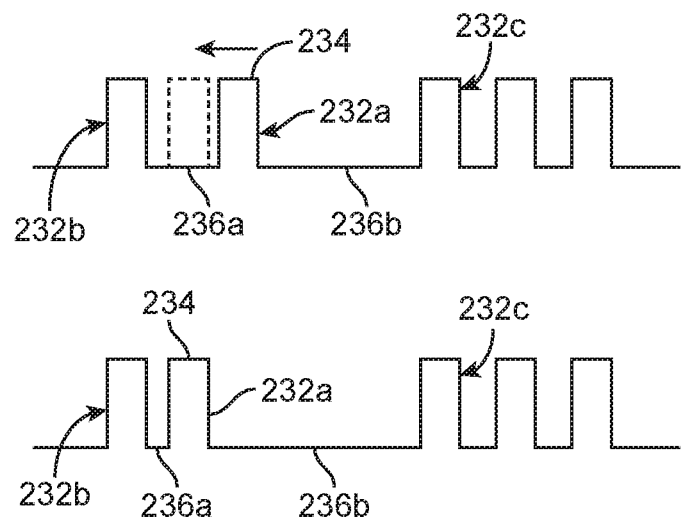
FIGS. 18 and 19 are plan views showing one technique for customizing an interpulse interval using the programming screen of FIG. 15.
Figure 19:
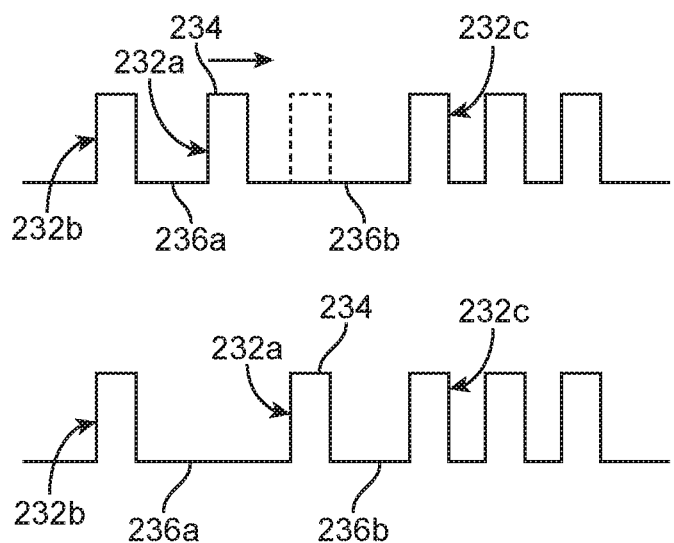

The pulse, interpulse interval, or inter-pulse group interval may also be modified directly in the pulse pattern display panel 204 by allowing the user to drag a portion of the displayed basis pulse pattern 212, repeating pulse pattern 214, or complete pulse pattern 216 using the appropriate pointing element (e.g., an actual pointing element or virtual pointing element). For example, the top line 234 of a selected pulse 232a may be dragged to the left to decrease the interpulse interval 236a between adjacent pulse 232b and the selected pulse 232a, while increasing the interpulse interval 236b between adjacent pulse 232c and the selected pulse 232a, as illustrated in FIG. 18. Similarly, the top line 234 of a selected pulse 232a may be dragged to the right to increase the interpulse interval 236a between the adjacent pulse 232b and the selected pulse 232a, while decreasing the interpulse interval 236b between adjacent pulse 232c and the selected pulse 232a, as illustrated in FIG. 19.

Figure 20:
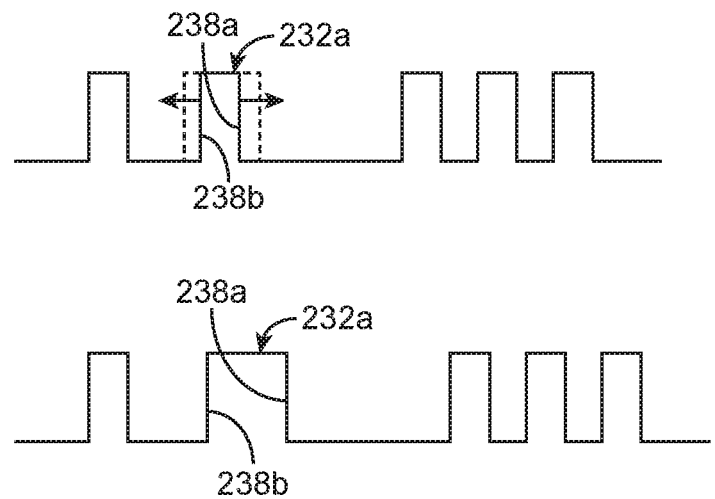
FIGS. 20 and 21 are plan views showing one technique for customizing a pulse width using the programming screen of FIG. 15.
Figure 21:
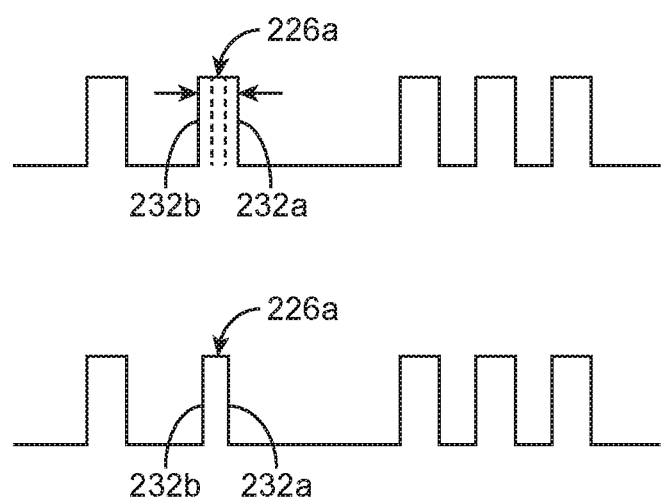

As another example, the right line 238a or left line 238b of the selected pulse 232a may be dragged outwardly from the center of the pulse 232a to increase the width of the selected pulse 232a, as illustrated in FIG. 20, or may be dragged inwardly towards the center of the pulse 232a to decrease the width of the selected pulse 232a, as illustrated in FIG. 21.

Figure 22:
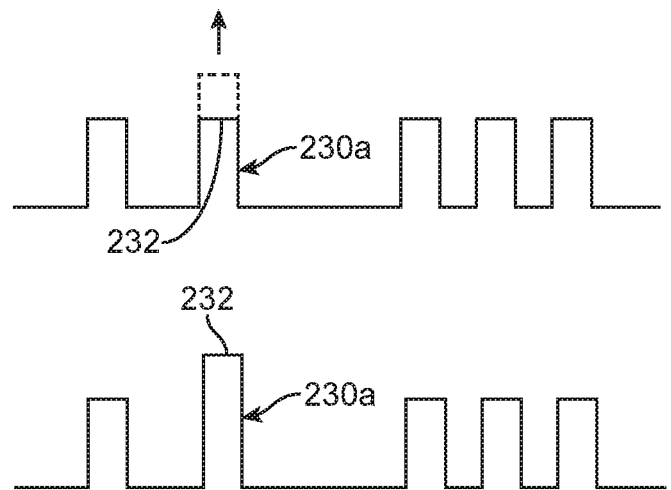
FIGS. 22 and 23 are plan views showing one technique for customizing a pulse amplitude using the programming screen of FIG. 15.
Figure 23:
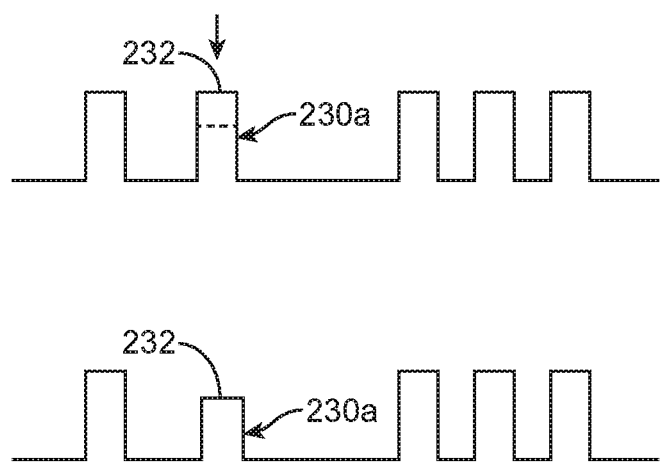

As still another example, the top line 234 of the selected pulse 232a may be dragged upward to increase the magnitude of the selected pulse 232a, as illustrated in FIG. 22, or may be dragged downward to decrease the magnitude of the selected pulse 232a, as illustrated in FIG. 23. Of course, all of the pulses of the displayed pulse pattern can be selected and subsequently modified in the same manner described with respect to the selected pulse 232a by dragging portions of these other pulses.

The lead display panel 206, much like the lead display panel 104, displays the graphical leads 128, graphical electrodes 130, and graphical case 132. In the illustrated embodiment, the polarity and fractionalized current values that were selected for the electrodes 130, 132 just prior to actuating the custom pulse pattern control 152 in FIG. 14 will be automatically selected in the lead panel 206 and associated with whichever of the pulses 224 that were selected in the pulse pattern display panel 204. Thus, electrode E2 has been selected as a cathode to which 100% of the cathodic current has been allocated, and electrodes E1 and E3 have been respectively selected as anodes to which 25% and 75% of the anodic current has been respectively allocated.

Of course, the polarity and fractionalized current values can be subsequently modified in the lead display panel 206. To this end, the pulse pattern customization panel 202 further includes an amplitude/polarity area 224 that comprises a graphical polarity control 226 having a "+" icon, a "−" icon, and an "OFF" icon, which can be respectively actuated to toggle the selected electrode 232, 234 between a positive polarization (anode), a negative polarization (cathode), and an off-state. The amplitude/polarity area 224 further includes an amplitude control 228, which includes an arrow that can be actuated to decrease the magnitude of the fractionalized current of the selected electrode 232, 234, and an arrow that can be actuated to increase the magnitude of the fractionalized current of the selected electrode 232, 234.

The pulse pattern customization panel 202 further includes a pulse customization completion control 230 that can be actuated to store the current customized pulse pattern in association with the number of the pulse pattern currently selected via the custom pattern select control 208 (in this case, the current customized pulse pattern will be stored as custom pulse pattern 3). Alternatively, the current customized pulse pattern will be stored if the custom pattern select control 208 is actuated to select a different custom pulse pattern number. Notably, if the time interval in the first nest or the time interval in the second nest has not been defined when the pulse customization completion control 230 has been actuated, these time intervals will be automatically defined using a suitable default value. Once a customized pulse pattern has been stored, another custom pulse pattern may be selected or defined in the manner described above.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for programming a neurostimulator to provide a neurostimulation therapy, comprising:
    customizing a pulse pattern for the neurostimulation therapy on a pulse-by-pulse basis in response to user input; and
    generating information for the neurostimulator, the neurostimulator configured to use the information to generate electrical stimulation energy in accordance with the customized pulse pattern for the neurostimulation therapy.

2. The method of claim 1, further comprising separately defining interpulse intervals between adjacent pairs of pulses in the pulse pattern in response to the user input.

3. The method of claim 1, further comprising separately defining widths of pulses in the pulse pattern in response to the user input.

4. The method of claim 1, wherein the neurostimulator includes a spinal cord stimulator, and customizing includes customizing the pulse pattern for a spinal cord stimulation therapy.

5. The method of claim 1, further comprising separately defining electrode combinations that deliver pulses in the pulse pattern in response to the user input.

6. The method of claim 1, further comprising adding or subtracting a pulse to or from the pulse pattern in response to the user input.

7. The method of claim 1, further comprising customizing the pulse pattern on the pulse-by-pulse basis by adjusting a multiplicative factor that is applied to a baseline stimulation parameter of the pulse pattern in response to the user input.

8. The method of claim 1, further comprising generating a program for an application specific integrated circuit to generate the customized pulse pattern.

9. The method of claim 1, further comprising displaying the pulse pattern, and customizing the pulse pattern based on user input corresponding to a drag, using a pointing element, of a portion of the displayed pulse pattern.

10. The method of claim 1, further comprising limiting the customizing of the pulse pattern in accordance with a set of heuristic safety/regulatory rules.

11. The method of claim 1, further comprising:
    in response to the user input, selecting one or more of a plurality of different customized pulse patterns stored in a memory; and
    generating information for the neurostimulator to deliver the electrical stimulation energy in accordance with the selected one or more of the plurality of different customized pulse patterns.

12. The method of claim 1, further comprising customizing another pulse pattern on a pulse-by-pulse basis in response to the user input, and generating information for the neurostimulator to deliver the electrical stimulation energy in accordance with the customized pulse pattern and to concurrently deliver electrical stimulation energy in accordance with the other customized pulse pattern in a respective timing channel.

13. The method of claim 12, further comprising defining a phase offset between the customized pulse pattern and the other customized pulse pattern within the respective timing channels in response to the user input.

14. The method of claim 1, further comprising globally modifying a stimulation parameter for a plurality of pulses of a tonic pulse pattern in response to the user input, and generating instructions for the neurostimulator to deliver the electrical stimulation energy to the patient in accordance with the tonic pulse pattern.

15. The method of claim 1, further comprising exporting the customized pulse pattern to a central database accessible to a plurality of users.

16. A non-transitory machine-readable medium including instructions, which when executed by a machine, cause the machine to program a neurostimulator to provide a neurostimulation therapy, including:
    customize a pulse pattern for the neurostimulation therapy on a pulse-by-pulse basis in response to user input; and
    generate information for the neurostimulator, the neurostimulator configured to use the information to generate electrical stimulation energy in accordance with the customized pulse pattern for the neurostimulation therapy.

17. The non-transitory machine-readable medium of claim 16, further comprising instructions, which when executed by the machine, cause the machine to:

define the interpulse intervals between adjacent pairs of pulses in the pulse pattern in response to the user input.

18. The non-transitory machine-readable medium of claim 16, further comprising instructions, which when executed by the machine, cause the machine to add or subtract a pulse to or from the pulse pattern in response to the user input.

19. The non-transitory machine-readable medium of claim 16, further comprising instructions, which when executed by the machine, cause the machine to:
   select one or more of a plurality of different customized pulse patterns stored in a memory in response to the user input;
   generate information for the neurostimulator to generate electrical stimulation energy in accordance with the selected one or more of the plurality of different customized pulse patterns.

20. A system for programming a neurostimulator to provide a neurostimulation therapy, the system comprising at least one device including processing circuitry, the system being configured to use the at least one device including processing circuitry to:
   customize a pulse pattern for the neurostimulation therapy on a pulse-by-pulse basis in response to user input; and
   generate information for the neurostimulator, the neurostimulator configured to use the information to generate electrical stimulation energy in accordance with the customized pulse pattern for the neurostimulation therapy.

* * * * *